US005088996A

United States Patent [19]

Kopfer et al.

[11] Patent Number: 5,088,996

[45] Date of Patent: Feb. 18, 1992

[54] ANTI-AERSOLING DRUG RECONSTITUTION DEVICE

[76] Inventors: Rudolph J. Kopfer, 1321 S. Eliseo Dr., Ste. 1, Greenbrae, Calif. 94904; Robert E. Smith, P.O. Box 2999, Ketchum, Id. 83350

[21] Appl. No.: 52,175

[22] Filed: May 18, 1987

Related U.S. Application Data

[63] Continuation of Ser. No. 600,504, Apr. 16, 1984, abandoned.

[51] Int. Cl.[5] ........................ A61M 5/32; A61M 5/00; A61M 37/00; B65D 8/32

[52] U.S. Cl. .................................... 604/415; 141/329; 141/330; 215/6; 215/247; 215/DIG. 3; 604/87; 604/411; 604/414; 604/416; 604/56

[58] Field of Search ........................ 604/56, 82, 83, 87, 604/88, 92, 125, 201, 407, 411, 414, 415, 416; 141/2, 19, 25–28, 329, 330, 369, 370, 372, 375, 383, 385, 386; 215/249, 247, 6

[56] References Cited

U.S. PATENT DOCUMENTS

| | | | |
|---|---|---|---|
| 2,554,352 | 5/1951 | Warp et al. | 604/148 |
| 2,642,064 | 6/1953 | Lawshe | 604/192 |
| 2,880,723 | 4/1959 | Adams | 128/215 |
| 3,052,241 | 9/1962 | Myerson et al. | 604/192 |
| 3,336,924 | 8/1967 | Sarnoff et al. | 128/272 |
| 3,375,825 | 4/1968 | Keller | 128/221 |
| 3,397,694 | 8/1968 | Ogle | 128/272 |
| 3,416,657 | 12/1968 | Sorensen, Jr. | 206/47 |
| 3,552,387 | 1/1971 | Stevens | 604/415 X |
| 3,563,373 | 2/1971 | Paulson | 206/63.2 |
| 3,578,037 | 5/1971 | Flynn | 141/330 X |
| 3,659,602 | 2/1972 | Cloyd | 128/220 |
| 3,682,174 | 8/1972 | Cohen | 604/201 X |
| 3,826,260 | 7/1974 | Killinger | 128/272 |
| 3,826,261 | 7/1974 | Killinger | 128/272 |
| 3,872,867 | 3/1975 | Killinger | 128/272 |
| 3,993,063 | 11/1976 | Larrabee | 128/215 |
| 3,995,630 | 12/1976 | van de Veerdonk | 128/218 DA |
| 4,020,836 | 5/1977 | Cunningham | 604/201 |
| 4,031,895 | 6/1977 | Porter | 128/272.1 |
| 4,089,432 | 5/1978 | Crankshaw et al. | 604/415 X |
| 4,180,070 | 12/1979 | Genese | 128/218 M |
| 4,187,893 | 2/1980 | Bujan | 215/247 |
| 4,194,640 | 3/1980 | Crankshaw et al. | 604/416 X |
| 4,312,349 | 1/1982 | Cohen | 141/330 X |
| 4,328,802 | 5/1982 | Curley et al. | 128/272.1 |
| 4,457,749 | 7/1984 | Bellotti et al. | 604/411 X |
| 4,516,967 | 5/1985 | Kopfer | 604/87 |
| 4,552,277 | 11/1985 | Richardson et al. | 604/411 X |
| 4,559,043 | 12/1985 | Whitehouse et al. | 604/201 |
| 4,564,054 | 1/1986 | Gustavsson | 141/329 |
| 4,614,515 | 9/1986 | Tripp et al. | 604/416 |
| 4,619,651 | 10/1986 | Kopfer et al. | 604/415 |
| 4,671,331 | 6/1987 | Pruden | 141/330 |

FOREIGN PATENT DOCUMENTS 126718 11/1984 European Pat. Off. .

Primary Examiner—Paul E. Konopka

Attorney, Agent, or Firm—Wood, Phillips, Mason, Recktenwald & Van Santen

[57] ABSTRACT

The present invention comprehends the provision of a fluid tight holding chamber which accumulates solution from the vial that aspirates during mixing or drawing fluid from the vial or is pressured out of the syringe upon extraction of the cannula from the vial. The holding chamber is defined in conjunction with the vial septum by a shield cap that surrounds and seals to the neck of the vial. The shield cap defines a guide for the cannula of the syringe and directs the cannula through a sealing member, the holding chamber, the septum and into the vial. One aspect of the invention provides a sleeve portion on the shield cap that receives and retains the syringe barrel. An arm is provided on the sleeve portion and has a notch that holds the syringe barrel in a predetermined position during shipment and storage of the assembly.

23 Claims, 4 Drawing Sheets

ANTI-AERSOLING DRUG RECONSTITUTION DEVICE

This application is a continuation, of application Ser. No. 600,504, filed Apr. 16, 1984, abandoned.

BACKGROUND OF THE INVENTION

1. Field Of The Invention

This invention relates to a syringe system for combining two dissimilar medicaments and, more particularly, to a structure for shielding a user of the syringe against aspirating or aerosoling the solution upon withdrawal of the syringe cannula from a mixing vial.

2. Background Art

It is known to reconstitute drugs by combining and mixing isolated, dissimilar medicaments immediately prior to patient infusion. This procedure is common with drugs that are unstable or deteriorate in solution. By isolating the ingredients, whether two liquids or a liquid and solid, the storage life of the drug can be extended.

Normally a sterilized, evacuated dose vial contains a crystalline component and is hermetically sealed by a pierceable septum. The syringe cannula penetrates the septum to establish communication between the vial chamber and the inside of the syringe barrel. The barrel retains a complementary diluent which is injected into the vial. The vial containing the two components is agitated to completely dissolve the solid. The reconstituted solution is drawn back into the syringe barrel for administration to a patient.

The problem which the present invention obviates arises during the mixing of the isolated medicaments. Complete evacuation of the vial before injection of the diluent is seldom realized. There is thus a residual pressure in the vial after the solution dose is extracted. This residual pressure often causes discharge of some of the remaining solution in the vial through the rupture in the septum made by the cannula. Where the drug is toxic, as is common in oncological treatments, or is otherwise dangerous, this escaping solution may pose a health hazard to persons preparing, administering and receiving the injection.

Protective shields associated with the vial to limit exposure to the solution during admixture are known. In the structure depicted in U.S. Pat. No. 3,336,924 to Sarnoff et al, cooperating cover parts encase the vial and define a chamber to closely, guidingly accept the syringe barrel. A seal between the barrel and cover is effected with the syringe fully seated. Upon partial withdrawal of the cannula from the vial, the medicament freely aspirates into the cover chamber and is confined by the leading edge of the barrel. With the syringe separated from the cover, the medicament is unrestrained, escapes through the chamber opening, which is as large as the barrel diameter, and poses a potential hazard to the syringe operator and/or the person disposing of the used, covered vial.

Another structure that exemplifies the state of the art is described in U.S. Pat. No. 3,659,602, to Cloyd. Cloyd discloses a two component syringe with separate vials penetrable by a double-ended cannula. An adapter sleeve is associated with one of the vials and defines a socket which accepts the end of a stopper piston. To operate the syringe, the vial and sleeve are advanced axially towards each other until the vial bottoms in the socket, thus eliminating the socket. Upon unseating the Luer taper from the adapter sleeve, the sleeve passage is open to the atmosphere. One contends in Cloyd with essentially the same problems associated with the Sarnoff et al structure previously described.

Another problem that the prior art structures make no provision for arises after filling the syringe. During aspiration of the solution from the vial into the barrel, air bubbles may become entrained in the solution. Before infusion, it is common to discharge a small volume of the solution to expel the bubbles. With the prior structures, this generally takes place with the cannula exposed to the environment and subjects the user once again to possible solution exposure.

Expulsion of the drug with the entrained air into the syringe cover in Sarnoff et al, while temporarily shielding the user, accumulates additional solution in the syringe cover in addition to that aspirating from the vial. Escape of the solution from the syringe cover is unobstructed so that once again the user and/or the person subsequently disposing of the vial and cover are liable to come into contact with the solution.

The present invention is specifically directed to overcoming one or more of the above enumerated problems known in the prior structures.

SUMMARY OF THE INVENTION

The present invention comprehends the provision of a fluid tight holding chamber which accumulates solution from the vial that aspirates or is pressured out of the vial upon extraction of the cannula from The vial or any time during the procedure of reconstitution. The chamber is defined in conjunction with the vial septum by a shield cap that surrounds the neck of the vial. The shield cap defines a guide for the needle hub and Luer lock sleeve on the leading portion of the syringe and directs the cannula through a sealing member the holding chamber, the septum and into the vial.

It is the principal objective of the present invention to provide a simple package that facilitates mixture of dissimilar medicaments and, which traps medicament solution that aspirates from the vial upon insertion or removal of the cannula to shield both a user during admixture and persons subsequently handling the vial package for disposal.

To accomplish this end, the shield cap and vial neck make fluid tight engagement. The shield cap has a penetrable wall portion to admit the cannula A sealing member lies in the cannula path in the shield cap and is self-sealing to confine the medicament in the holding chamber after the syringe is withdrawn.

The holding chamber can additionally be used to receive the expelled solution with entrained air bubbles before infusion. By partially backing out the syringe, the cannula provides a communication conduit between the holding chamber and the barrel reservoir. The discharged solution is captured in the chamber so that it does not pose an external health hazard.

To consistently seat the Luer lock sleeve and to direct the cannula through the vial septum, a guide cavity is provided at the syringe-receiving end of the shield cap. The guide cavity guides the needle and needle hub so that the shield cap and syringe are self-aligning.

It is another aspect of the invention to provide an improved sealing structure between the shield cap and the vial neck. The shield cap has a mating cylindrical portion with an imperforate ring at its free end and a radially inwardly projecting annular rib associated with the ring. The cylindrical portion is slit axially from the ring to permit lengthwise compression of the cylindrical portion to allow for sufficient radial expansion to pass the rib over an enlarged rim on the neck of the vial bottle. With the rib seated behind the rim, a compression ring is disposed over the cylindrical portion to compress the rib radially inwardly to bear the same against the vial. Removal of the shield cap is prohibited with the compression ring in place. The compressed annular rib causes a redundant fluid tight seal to be effected between the shield cap and the vial. In one form of the invention the compression ring interengages with one way notches to prevent removal of the ring and therefore to prevent removal of the vial from the shield cap. Other methods of sealing structure may be effective but the end result is the same.

DETAILED DESCRIPTION OF DRAWINGS

Figures 1, 2:
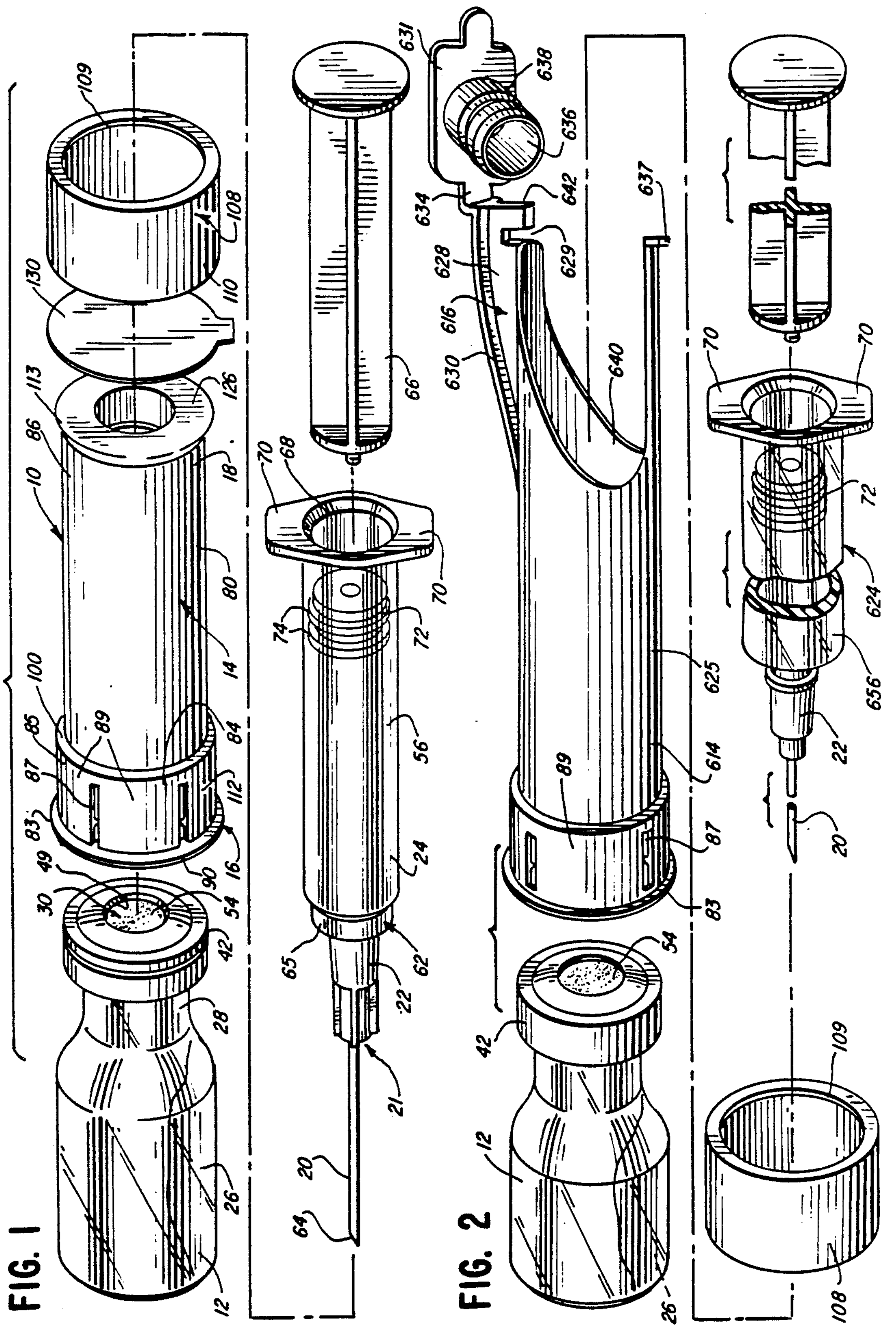
FIG. 1 is an exploded perspective view of a conventional vial operatively associated with a first type of shield cap according to the present invention.
FIG. 2 is an exploded perspective view of a conventional vial operatively associated with a second type of shield cap according to the present invention.
Figures 3, 4, 5:
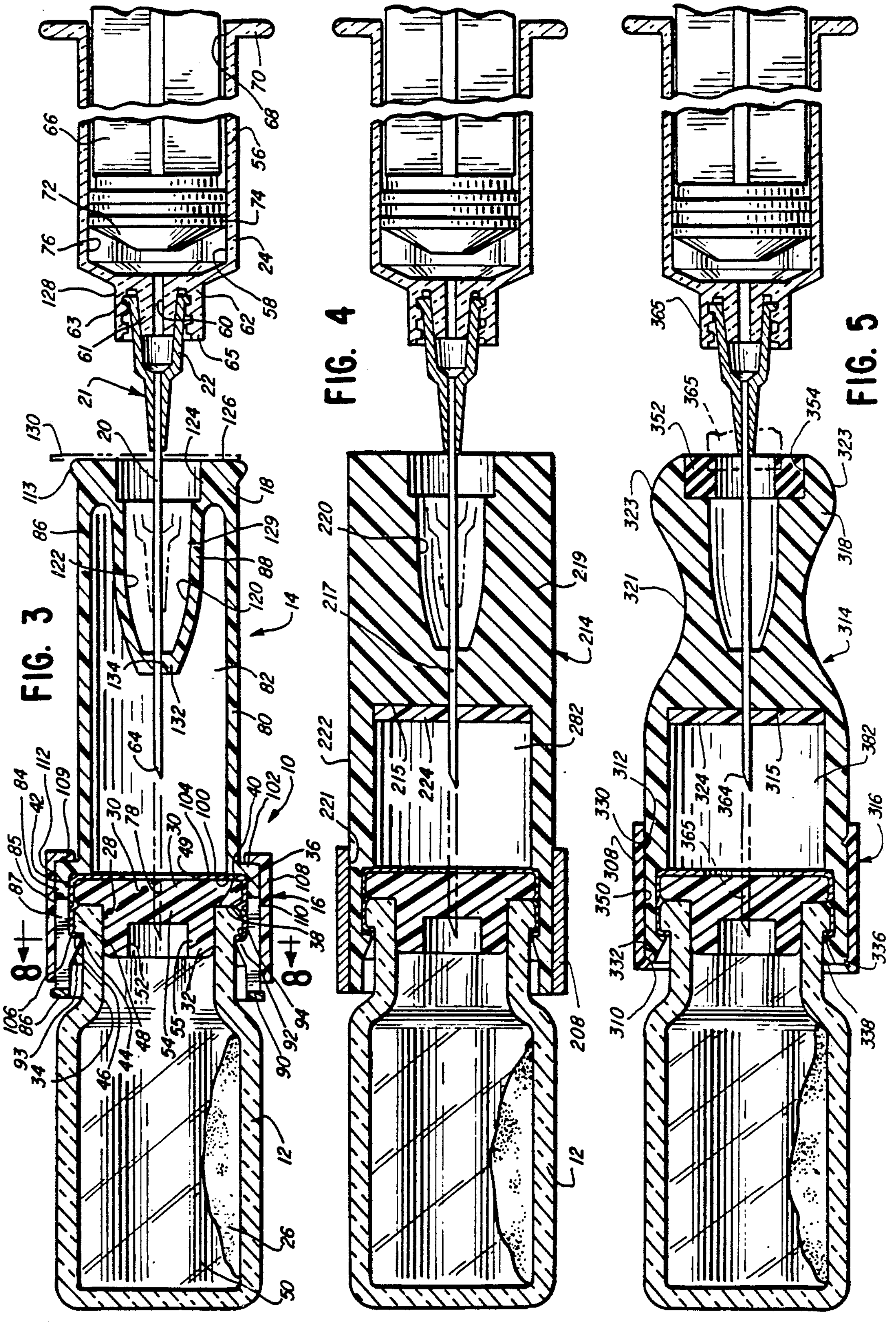
FIG. 3 is a sectional view of the vial, shield cap and syringe of FIG. 1 only in assembled condition with the syringe needle partially inserted into the shield cap.
FIG. 4 is a sectional view similar to that in FIG. 3 with a third type of shield can according to the present invention.
FIG. 5 is a sectional view as in FIGS. 3 and 4 with a fourth type of shield cap according to the present invention.

FIGS. 1 and 3 illustrate a system embodying the present invention and comprises generally a vial package 10 comprising a glass dose vial 12 and a shield cap at 14 united with the vial 12 through a telescoped connection at 16. The syringe end 18 of the shield cap is adapted to accept a cannula 20 of a needle 21 and a Luer taper on the cannula hub 22 at the leading portion of a conventional syringe 24.

Throughout the description of the invention, like reference numerals will be used to identify the vial 12 and syringe 24 which are conventional in construction and identical in each of FIGS. 1-8, 11 and 12. The modifications to the vial package 10 comprehended by the invention, focus on the shield cap 14.

Before the invention can be appreciated, the basic vial and syringe structures will be described as well as the mixing operation for which the invention is particularly suitable.

The vial 12, which is generally made from glass, is sterilized and contains a measured supply of solid form medicament 26. The open end 28 of the vial is sealed by a resilient stopper 30 having a body 32 that is squeezed into the cylindrical neck opening 34. The body 32 has an integral, enlarged top 36 defining a shoulder 38 sealingly abutting the free edge 40 of the vial 12.

A thin, deformable metal seal 42 surrounds the top 36 and an enlarged rim 48 on the neck 34 of the vial and is crimped to deflect its free edge 44 behind a shoulder 46 defined by the rim 48. The seal 42, as it is crimped, compressibly draws the top 36 against the vial to hermetically seal the vial chamber 50. The cap has a circular cutout 49 to permit access to the stopper by the needle cannula as described below.

The stopper 30 has a cylindrical cavity 52 which establishes communication between the barrel of the syringe 24 and the vial before full penetration by the cannula. The cavity reduces the axial dimension of the septum at the central portion of the stopper 30 to facilitate penetration by the cannula, and also reduces the thickness of annular wall 55 so that it is more readily deformable upon insertion of the stopper 30 into the vial.

Briefly, the syringe 24 is conventional and comprises a barrel 56 defining an internal, liquid retaining reservoir 58 which communicates with the needle 21 through a capillary 60 in a Luer-tapered tip 61 of a Luer-lock type connector 62. The needle 21 has the cannula 20 seated at one end in a female Luer-tapered hub 22 which hub has a locking flange 63 for locking in the sleeve 65 of connector 62. The cannula 20 has a tapered penetrating tip 64.

To effect discharge of liquid through the barrel, a plunger 66 is depressed from the open end 68 of the barrel, toward the cannula. This is accomplished by grasping finger flange 70 with the index and middle fingers, situating the thumb on a rest (not shown) at the end of the plunger and drawing the thumb towards the fingers. A rubber piston or stopper 72 is fit at the end of the plunger and is suitably attached to follow the plunger movement. The stopper 72 has annular ribs 74 which closely sealingly conform to the inside surface 76 of the barrel 56. As the plunger is depressed, the stopper compresses the liquid in the reservoir, forcing the discharge of the solution through the cannula 20.

According to the prior art, to carry out the mixing operation, a measured supply of liquid solvent is drawn into the barrel 56. In the alternative the syringe may be prefilled and packaged in a sterile container. The syringe is advanced toward the vial to that the cannula pierces the septum 54 and establishes communication with the vial chamber 50 which contains the solid component. The liquid supply is then injected by depressing the plunger and the vial shaken to dissolve the powder. The reconstituted solution is extracted by withdrawing the plunger.

Reasonably complete evacuation of the vial before sealing is striven for. However, in practice, only partial evacuation is achieved. Upon injection of the liquid component from the syringe, pressure is developed in the vial. A residual pressure is often maintained after the withdrawal of the fluid into the syringe, and is significant particularly when less than the entire amount of solution is withdrawn from the vial. The residual pressure can cause a discharge of the solution through the rupture 78 in the stopper made by the insertion of the cannula, particularly as the cannula is being withdrawn from the stopper. The solution may be expelled until the pressure in the vial is reduced sufficiently that the self-sealing nature of the stopper obstructs its passage.

The present invention is primarily directed to capturing the solution aspirating from the vial during and after withdrawal of the cannula from the stopper. The shield cap 14 disclosed in FIG. 1 comprises a cylindrical body 80 defining an internal holding chamber 82 with a vial end 84 and syringe end 86.

The vial end 84 of the shield cap 14 has an enlarged diameter connecting portion 85 that is open to accept the neck of the vial. The connecting portion has slits 87 extending axially from a continuous collar 83 at the free edge 90 to a point spaced axially from the internal shoulder 100 forming the junction between the connecting portion 85 and the body 80 of the shield cap 14. The slits 87 divide the connecting portion into plural segments 89, FIGS. 1 and 8. Spaced axially of the collar 83 and projecting radially inwardly from the wall of each segment 89 is a rib 92, which rib is annular with the exception of the breaks caused by the slits 87. The rib 92 has a ramp surface 93 which constricts the opening in the connecting portion and defines a shoulder 94 facing toward the syringe end of the cap at the radially thickest portion of the rib 92.

Figures 6, 7, 8, 9, 10:
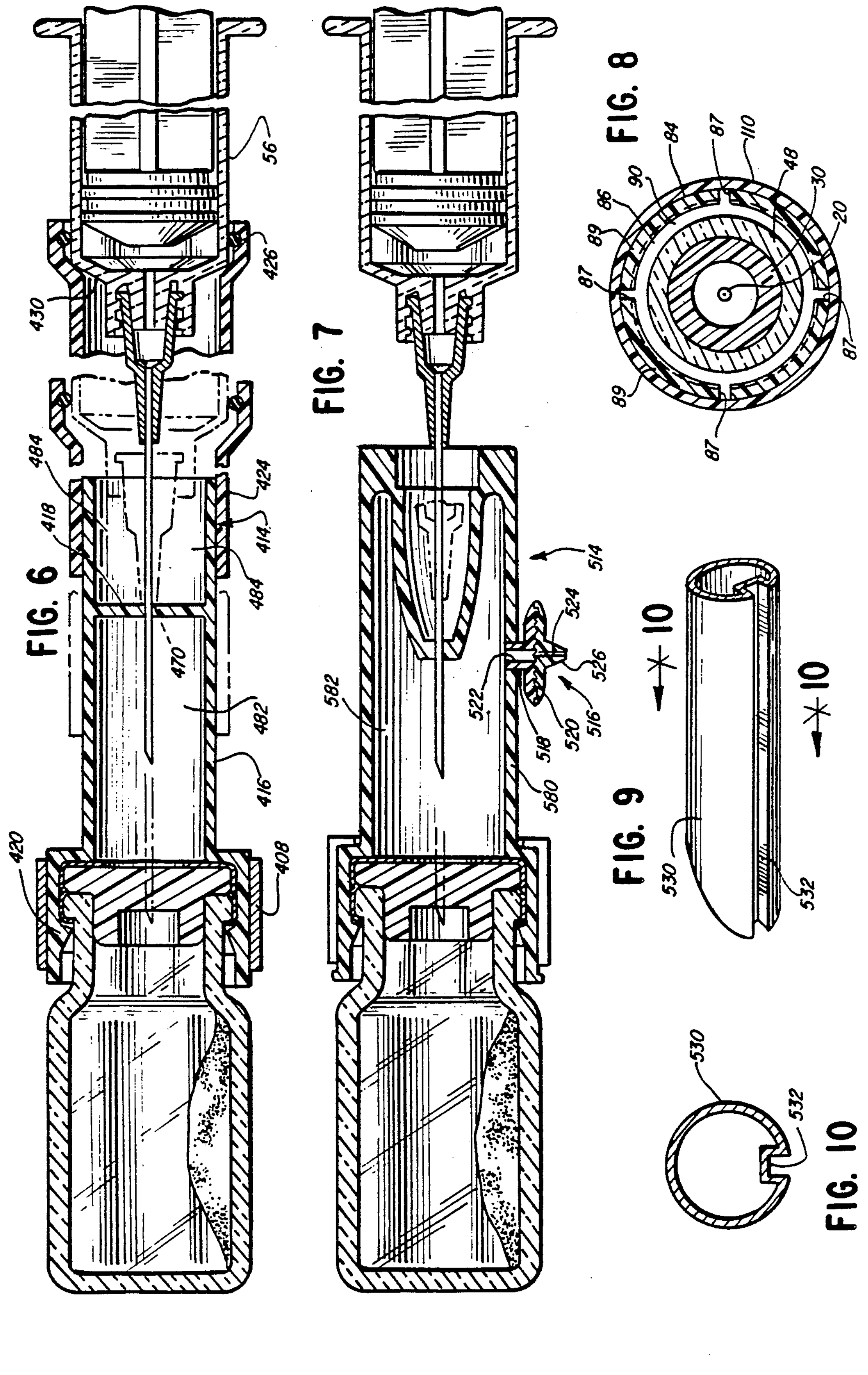
FIG. 6 is a sectional view similar to that in FIGS. 3-5 with a fifth type of shield cap according to the present invention.
FIG. 7 is a sectional view similar to that in FIGS. 3-6 with a sixth type of shield cap according to the present invention.
FIG. 8 is a sectional view of the connection between the vial and the shield cap along line 8—8 of FIG. 3.
FIG. 9 is an enlarged, fragmentary perspective view of a modified form of syringe needle for use with the shield cap of the type shown in FIG. 7.
FIG. 10 is a sectional view of the needle along line 10—10 of FIG. 9.

To assemble the shield cap 14 and vial 12, the connecting portion 85 of the cap and the stopper end of the vial are axially aligned and advanced, one toward the other. The seal 42 about the vial neck is closely surrounded first by the collar 83 of the connecting portion 85. As the connecting portion is advanced toward the vial, the ramp surface 93 on the rib 92 encounters the metal seal and is deflected along with the segments 89 radially outwardly sufficiently to allow passage of the rib. To facilitate this expansion and also the sealing as hereafter described, the plurality of slits 87 between the segments 89, as seen most clearly in FIGS. 1 and 8, are provided. The slits 87 end short of the shoulder 100 forming the end of the connecting portion so is not to compromise the seal between the vial and the holding chamber. The slits 87 permit radial collapsing of the connecting portion of the cap, relaxing the material about the rib 92 so that the rib can position itself beneath the overhang of the seal on the neck of the vial.

The shield cap 14 is fully seated of the vial when the shoulder 100 defined by a radial offset 102 between the body 80 and the enlarged diameter connecting portion 85, abuts the facing surface 104 of seal 42. With the cap and vial in the described relative relationship, the shoulder 94 on the rib 92 axially intersects a rounded portion 106 on the corner of the rim 48.

To further secure the shield cap and vial, a cylindrical locking ring 108 is provided and has a radially inturned flange ring portion 109 which guides the ring 108 axially along the body and abuts the offset 102 to establish the fully seated ring position. The ring 108 has a main, cylindrical portion 110 with an inside diameter slightly less than the diameter of the outside surface 112 of the connecting portion 85 of the shield cap with the connecting portion positioned over the vial neck.

The locking ring is brought into axial overlapping relationship with the connecting portion 85. As this occurs, the connecting portion of the cap is compressed radially, which action is accommodated by the slits 87. With the ring in a fully seated position, the rib 92 is forced against the neck of the vial beyond the rounded portion 106 which tends to stretch the connecting portion 85 and closely captures the combined thickness of the seal 42 and the stopper top 36 to still further enhance the seal therebetween. Separation of the cap and vial is precluded as long as the compression locking ring 108 is in position around the connecting portion. A shoulder 113 is integrally molded on the syringe end 86 of the shield cap and is intended to retain the locking ring 108 on the shield cap. During assembly [he flange 109 on the locking ring is forced over the shoulder 113. Once the flange 109 is deflected over the shoulder it will return to its original dimension.

The cap and locking ring 108 are preferably made from a moldable material that is deformable sufficiently to facilitate the aforementioned connection between the cap and vial. The material should be resilient enough to maintain a leakproof seal at the point of abutment between the shoulder 100 defined by the offset and the cap surface 104. Further, the material should be capable of establishing a seal about a penetrating cannula. The material should self-seal the rupture made by the cannula with the cannula withdrawn. The significance of this particular feature is elaborated below.

The syringe end 18 of the shield cap 14 has an integral, truncated, parabolic shaped internal seal portion 88, offset axially into the chamber 82 and defining a cavity 120 opening away from the vial end for accepting the leading portion of the needle and syringe. A sealing member 132 forms the truncated part cf the seal portion 88.

The cavity 120 is defined primarily by the inner surface 122 of the parabolic portion 88. The inner surface 122 is shaped to provide clearance between the hub 22 of the needle. An enlarged cylindrical recess 124 defines the entrance to the cavity 120 to accept a portion of the cylindrical outer surface 128 of the sleeve of the Luer-lock connector on the syringe. The seal portion 88 defines one wall of the holding chamber 82 with another wall being the cylindrical body 80. One end of the holding chamber is defined by the end of the shield cap with the other end being defined by the end of the vial as it is sealed to the shield cap.

The walls of the recess 124 and cavity 120 cooperatively guide the cannula, syringe hub and Luer-lock sleeve 65 into a fully seated position in the cap. The relationship between the shield cap and the hub 22 makes it possible for the portion 88 of the shield cap to grip the hub 22 whereupon twisting of the syringe relative to the shield cap will assure a firm lock between the hub and syringe. Ribs 129 formed on the surface 122 of portion 88 enhance the gripping of the hub.

The vial package, including the shield cap and vial, can be sold as an assembled unit. To prevent contamination of the cavity 120, a sterile, protective sealing sheet 130 is used to cover the free edge 126 of the cap and is bonded thereto as by the use of a adhesive. The end of the shield cap can be closed and sealed by a tethered flip top configuration of the type shown in FIG. 11.

The operation of the device is as follows. Initially the sheet 130 is peeled off the shield cap. A syringe 56 filled with medicament and with the cannula of the needle unsheathed has the cannula 20 introduced through the cavity 120 and penetrates the sealing member 132. The cannula is directed through the holding chamber 82 and pierces the septum 54 to establish communication between the vial chamber 50 and the syringe reservoir 58. The hub 22 and the Luer-lock sleeve 65 is respectively in the cavity 120 and recess 124 with the Luer-lock sleeve bottomed on the abutting surface between the cavity 120 and recess 124.

Upon depressing the plunger to force the fluid from the reservoir into the vial, pressure is developed in the vial, some of which may aspirate past the cannula into the holding chamber 82. The vial package 10 with the inserted syringe is then shaken to mix the medicaments. Upon completing the mix, the plunger s withdrawn to fill the reservoir 58 with the reconstituted medicament. As the cannula is withdrawn, aspirating of the mixture may occur past the outside of the cannula and into the holding chamber. Upon withdrawal of the cannula, residual pressure may still exist in the vial, which may be substantial if the volume of solution that was introduced is not entirely withdrawn or if a buildup of gas occurs in the vial. At this point, some of the remaining solution under pressure may aspirate into the holding chamber through the puncture 78 in the stopper. All asperated solution is completely captured in the holding chamber 82.

The holding chamber 82 can also be used to expel air bubbles entrained in the solution that is withdrawn from the vial. To accomplish this, the point 64 of the needle is retained in the holding chamber 82 as depicted in solid lines in FIG. 3. The syringe, shield cap and vial are inverted with the vial uppermost so that the air will accumulate at the needle end of the syringe barrel. The plunger is then depressed to expel a small amount of solution and all of the air bubbles into the holding chamber thereby eliminating the bubbles from the barrel. Thereafter, the needle is withdrawn from the shield cap ready for use on a patient. The shield cap and vial with the accumulated aspirated solution confined positively in the holding chamber can be safely handled and disposed of without contamination of the handlers.

Several modifications to the invention are disclosed in the remaining figures. In FIG. 4, a shield cap 214 is shown assembled with a vial 12 and adaptable for use with a syringe 24. Both the vial and syringe are identical to those disclosed in FIG. 1. The shield cap 214 is formed with a cavity 220 similar in shape and function to cavity 120 in FIG. 1. However, the shield cap 214 is substantially solid along its axial coincidence with the cavity 220 whereas in FIG. 3 the chamber 82 has an annular expansion about the cavity. A bore 217 is provided through the solid portion 219 of the cap to provide a communication path between the chamber 220 and a holding chamber 282. The bore 217 guides the cannula to assure coaxial alignment between the syringe and the cap.

The connecting portion 216 of the cap is substantially identical to that in FIGS. 1 and 3. However, rather than the stepped diameter construction between the body 80 and the connecting portion 16 of the cap in FIGS. 1 and 3, the cap in FIG. 4 has a constant diameter along its length. A locking ring 208 operates in the same manner as locking ring 108 in FIGS. 1 and 3, however since the entire inside surface 221 of the ring mates closely with the outside surface 222 of the cap 214, there is no corresponding guiding ring associated with the ring 208.

An additional feature of the construction in FIG. 4 is the provision of a sealing member or sealing layer 224 seated against the end wall 215 of the chamber 282. The sealing member 224 appears as a cylindrical disc and is made preferably from a rubber material that has good self-sealing characteristics. Because the sealing member 224 is provided, the material making up the remainder of the cap need not be self-sealing. The sealing member 224 is fastened to the wall 215 by means of adhesives, ultrasonics or the like.

The shield cap 314 in FIG. 5 is configured similarly to the arrangement in FIG. 4. The primary distinction is that the corresponding solid portion 319 has a curved, reduced diameter middle section 321 which facilitates grasping between a user's fingers. The corners 323 toward the syringe end 318 of the cap are curved for user comfort. The particular cap configuration, in addition to facilitating grasping, also reduces the amount of material required to make up the cap. Substantial cost reduction is realized, particularly when the cap is molded from plastic, as is preferred. A sealing member 324 is seated in the holding chamber 382 against the wall 315.

Another distinction in the FIG. 5 embodiment is the slight modification of the connecting portion 316. With the shield cap 314 in place, a locking ring 308 is assembled. The ring 308 has axially spaced wedge-shaped, annular rings 310,312 extending radially inwardly from the inside ring surface 350. The ring 312 seats in a cooperating groove 330, on the cap 314. Simultaneously, one wall 332 of the ring 310 bears against a bevelled surface 336 adjacent the free edge 338 of the cap.

A further modification to the cap 314 in FIG. 5 is the provision of a resilient annular seal 352 in a recess 354 at the syringe end 318 of the cap. The seal 52 readily deforms to the contour of the Luer-lock connector sleeve 365. The seal 352 is primarily for use with units where the syringe is prefilled and is included as a package with the vial and shield cap. The cannula tip 364 will be seated in the stopper 330 with the seal 52 engaging the forward part of the Luer-lock connector sleeve 365. When the device is ready for use, the syringe is pushed toward the shield cap to complete the penetration of the cannula into the vial.

The FIG. 6 embodiment has a shield cap 414 with a cylindrical body 416 having an intermediate partition 18 separating a holding chamber 482 and hub receiving chamber 484, with the latter loosely accepting the entire leading portion of the syringe. The body 416 is formed (molded or the like) of material with sufficient memory that the partition 418 is the sealing member which is punctured by the cannula when the syringe is assembled with shield cap 414. The puncture in the sealing member will seal when the cannula and syringe are separated from the shield cap 414. The body 416 is integral with an enlarged diameter vial end 420 which connects in similar fashion to the vial end 84 in FIGS. 1 and 3 and is surrounded by a compression locking ring 408 like that shown in FIG. 4.

An additional sleeve 424 is provided and telescopingly mates with the body 416. The sleeve 424 defines a rearwardly opening groove 426 at its free end. An O-ring 428 is seated in the groove 426 and seals between the sleeve and a tapered wall 430 at the leading edge of the barrel 56. The 0-ring 428 is preferably fixed to both the sleeve and barrel to make a unitary structure therewith.

The sleeve 424 positively guides the syringe relative to the vial with the attached cap 414. Movement of the syringe toward the vial is arrested as the free edge 470 of the hub abuts the partition 418 as shown in phantom.

A problem that is ofttimes encountered during a mixing operation is the build-up of pressure in the vial. While this normally does not occur with the syringe operated by a skilled technician, the pressure build-up is a problem that must be dealt with. To solve this pressure build-up problem, the FIG. 7 adaptation is appropriate.

In FIG. 7, a shield cap is shown at 514 that is substantially the same as that depicted in FIGS. 1 and 3. The structure is modified by providing a bleeder vent at 516 which may be formed integrally with the cap or manufactured as a separate unit to be assembled therewith. The vent 516 comprises a cylindrical conduit 518 which penetrates the wall of the body 580. An enlarged disc-shaped chamber 520 is formed and is in fluid communication with a passage 522 and a passage 524 through a discharge head 526. Within the chamber 520 a filter element is disposed which may be a hydrophobic filter or an appropriate filter for filtering out the medicament aspirated into the holding chamber 582.

The FIG. 7 invention also contemplates the use of a modified form of cannula 530, the details of which are clearly shown in FIGS. 9 and 10. The cannula has an integrally formed, radially inwardly directed, vent channel 532. The channel 532 provides a bleed path with the cannula inserted through the vial septum. In spite of the self-sealing nature of the stopper, the pressure equalizes through the bleed path on opposite sides of the interface with the cannula in place. If the equilibrium pressure is greater than atmospheric pressure the pressure will release through the vent structure 516, which filters any harmful impurities that might otherwise expel into the environment.

It should be understood that this particular modification of the cannula 532 might be used with the shield caps of the prior embodiments. In most operations however, the holding chambers 82,282,382,482 are of sufficient volume to allow pressure equalization on opposite sides of the stopper.

Figure 11:
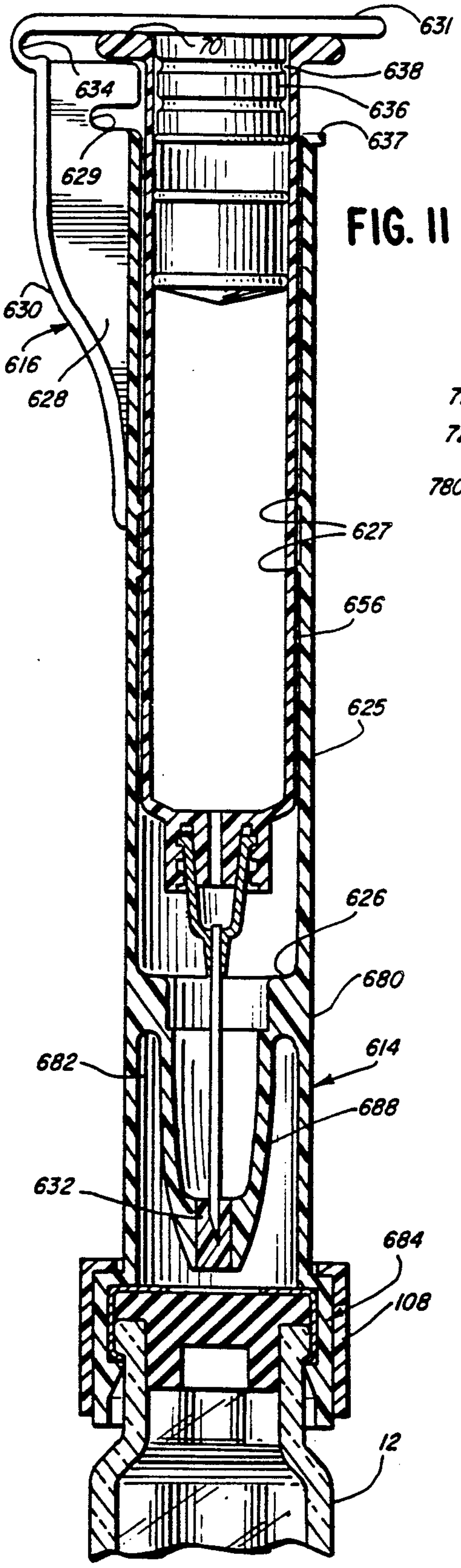
FIG. 11 is a sectional view of the form of invention shown in FIG. 2 only with the parts assembled together in a stored or shipping condition.

FIGS. 2 and 11 show still another form of shield cap 614 as an integral part of a preloaded syringe apparatus. The syringe cap 614 has a syringe plunger positioning arm 616 for retaining a flange 70 of a preloaded syringe 624 in a predetermined position during shipment and storage without plunger rod 666 attached Specifically, the shield cap 614 has a slotted vial end portion 84 similar to vial end portion 84 of FIGS. 1 and 3. A seal portion 688 is provided in the cylindrical body 680 and has a sealing member 632 closing the inner end thereof. The seal portion 688, cylindrical body 680 and the sealed end of the vial 12 define the holding chamber 682. The cylindrical body 680 is elongate and extends considerably beyond the end 626 of the seal portion 88 to form a retaining sleeve portion 625 which has spaced inwardly disposed concentric ribs 627. The syringe plunger positioning arm 616 is integrally formed as an extension of one segment of the sleeve portion 625 and has a radially outwardly formed web 628 with a retaining notch 629 near the outer end thereof for holding flange 70 in the syringe activated position. A flange 630 is formed outwardly in both directions from the positioning arm 616 to add stiffness to the arm. A closure 631 is tethered by a web 634 to the arm 616 and has a cylindrical plug 636 projecting from one face thereof. Concentric sealing ribs 638 are formed on the outer surface of the plug.

The vial end 684 is sealingly attached to a vial 12 having a powdered medicament 26 therein by means of the slots 87, segments 89, ring 83 and sleeve ring 108 as described with respect to FIG. 3. A syringe 624 is preloaded with a second medicament in front of the stopper 72 whereupon the syringe with the needle assembly 21 attached thereto is advanced into the open end 640 of the sleeve portion 625 of the seal cap 614 until the end of the needle cannula 20 is embedded in the sealing portion 632. The barrel 656 of the syringe will be sealed in the sleeve portion 625 by the ribs 627 which can be used to maintain the unembedded part of the needle cannula 20 in a sterile condition and to add resistance to relative movement between the sleeve and the syringe. The flange 70 on the syringe barrel is positioned against the tooth 642 on the end of the arm 616 when the end of the needle is properly positioned in the sealing portion 632. The closure 631 is pivoted to seat the plug 636 in the end of the syringe barrel and holds plunger 72 in position. A plunger rod 666 is taped or otherwise secured or attached to the assembly during storage and slipment.

To prearm the assembly prior to patient use, the closure 631 is pivoted to remove the plug from the syringe barrel. The plunger rod 666 is threaded (or otherwise connected) to the plunger 72. The arm 616 is urged radially outward to clear the flange 70 whereupon the syringe barrel and needle are urged forward to penetrate the needle through seal 632 and into and through seal 54 of the vial. The flange 70 will seat in the notch 629 and will hit syringe flange stop 637 whereupon the assembly is prearmed.

The medicaments are mixed and the syringe is removed from the sleeve portion 625 ready for injection following the same techniques as described heretofore in reverse order.

Figure 12:
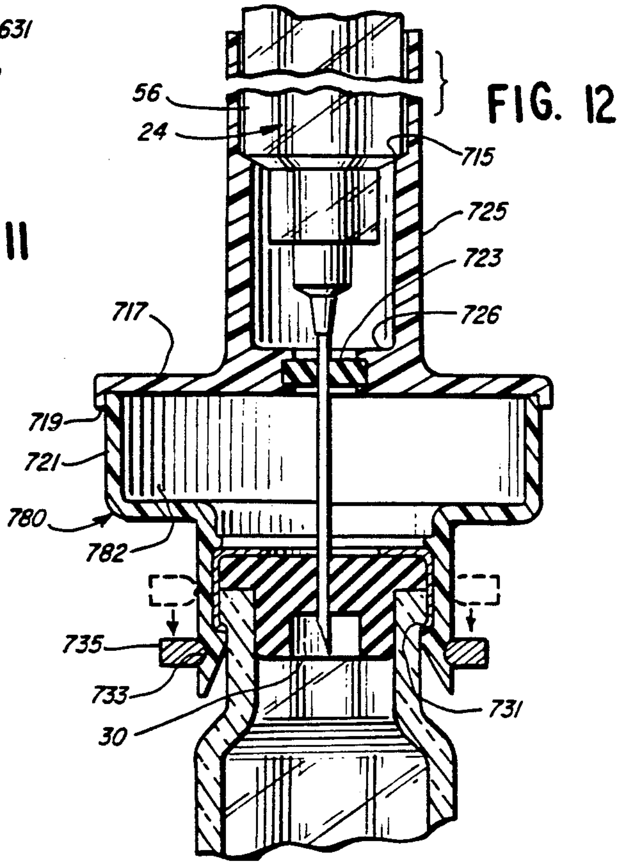
FIG. 12 is a sectional view similar to FIG. 3 with a seventh type of shield cap according to the present invention.

FIG. 12 illustrates an assembly wherein the holding chamber 782 is enlarged to provide an enlarged expansion chamber for the aspirating medicaments. The shield cap assembly 714 has a sleeve portion 725 for receiving the barrel 56 of the syringe 24 and includes a shoulder 715 serving as a stop for the syringe barrel. A flange 717 flares outward of the sleeve portion and has a downturned edge 719 sealed against a wall 721 of a body 780. The body 780 has a cylindrical hub 723 axially aligned with the sleeve portion 725. A rib 726 is formed internally of the one end of the sleeve portion which rib supports a self-sealing puncturable seal 727 The cylindrical hub 723 has a tapered exposed end 729 which terminates in an inturned shoulder 731 which seats behind the seal end 42 of a vial 12. A groove 733 is formed around the outer face of the hub 723 in which a sliding ring 735 seats to hold the shield cap 714 assembled in sealing relationship on the vial.

The syringe 24 is inserted in the sleeve 725 with the needle penetrating through the seal 727 and through the seal 30 in the vial. The medicaments are mixed, the aspirated medicament is trapped in the expansion chamber 782 as described hereinabove.

Figure 13:
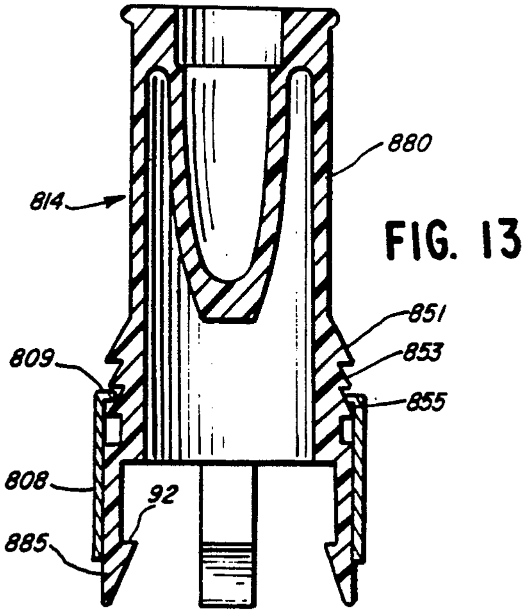

FIG. 13 illustrates a shield cap assembly 814 all as described above with respect to FIGS. 1 and 3 with the addition of an improved positive structure for locking the shield cap to the vial against removal. The vial end 884 has plural axially spaced rows of notches 851, 853,855 which may be continuous about the shield cap or may be short circumferential segments. The notches are formed on the cylindrical body 880 axially of the connecting portion 885. The locking ring 808 encircles the cylindrical body and has an inturned flange 809. The diameter of the inner edge of the flange 809 is slightly larger than the outside diameter of the cylindrical body 880 but is smaller in diameter than the outer end portions of the notches 851,853,855. With the connecting portion 885 of the shield cap assembled over the end of a vial 12, the inturned ribs 92 seat beneath the enlarged head on the vial. The locking ring 838 is slid axially over the connecting portion 885 with the flange 809 snapping over successive notches 851,853 and possibly 855 until the shield cap is securely located on the vial. The flange 809 on the ring 808 once past notches 851,853,855 cannot be backed past any one of said notches, thus locking the shield cap permanently to the vial.

It is of course understood that the locking arrangement for the shield cap of FIG. 13 could be used with the shield cap of FIGS. 1 through 12 and vice versa. Also the sleeve portion 625 and retaining arm 616 of FIG. 11 could be used with the shield cap of FIGS. 1-10, 12 and 13. Various combinations of the novel features shown and described are within the scope of the invention herein disclosed. Other methods of securing the vial may be used and we are not limiting the device to this method.

Figure 14:
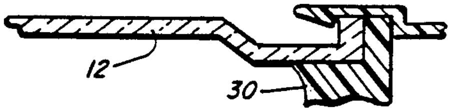
FIG. 13 is a sectional view of a modified form of connection between a shield cap and a vial and FIG. 14 is a partial sectional view of another modified form of connection between a shield cap and a vial.

In the preloaded form of FIGS. 2 and 11, it may not be necessary to seal the vial with the ring seal 108, but the shield cap can be made of a more rigid material in order that it can be jam fitted over the vial neck and vial stopper to cause a perfect seal with or without the use of the aluminum band. In this instance, it may be necessary to have a more penetrable seal 632, (see FIGS. 14 and 11).

The compression ring seal 108 can be elongated toward the syringe end so as to allow safety to the user in the event that the cannula mistakenly penetrates the wall of the shield cap 14,214,314,414,514,614.

It should be understood that the foregoing description was made for purposes of clarifying the structure and operation of the invention, with no unnecessary limitations to be understood therefrom.

We claim:

1. A shield structure for preventing exposure to a solution aspirating from a chamber in a vial that has a septum which is penetrable by a cannula on a syringe which is usable to withdraw solution from a vial and deliver withdrawn solution to a patient, said cannula being attached to a barrel of a syringe to establish communication through a puncture opening in the septum made by said cannula between the inside of the vial and a fluid retaining reservoir defined by the syringe barrel, said shield structure comprising:

a body portion having a vial end, a syringe end, and a surface between the ends of the body portion defining an internal fluid holding chamber, said body portion having an opening in the vial end in communication with said chamber;

means for connecting the body portion to a vial so that a vial septum sealingly closes the opening in the body portion and the surface of the body portion and septum cooperatively bound and make fluid tight the holding chamber; and second means at the syringe end of the body portion for removably, sealingly admitting the cannula with the attached barrel into said fluid tight internal holding chamber and for resealing the holding chamber upon the removal of the cannula from the fluid tight internal holding chamber and separation of the cannula from the body portion so that said cannula with the attached barrel can be moved relative to the body portion and vial for passage through said second means, the fluid tight internal holding chamber, the septum and into the vial, the passage of the cannula through the septum forming a puncture opening in the septum to establish communication between the barrel and vial, whereby said cannula with the attached barrel can be removably directed into the vial to reconstitute in and withdraw medicament in the vial from the vial and into the barrel;

said syringe being separable as a unit consisting of the barrel and cannula from the vial and entire shield structure for administration of the solution to a patient in conventional manner so that any solution remaining in the vial that aspirates through the puncture opening upon the cannula withdrawing from the septum is substantially confined in the fluid tight internal holding chamber, thereby protecting the user of the syringe from exposure to the aspirating solution.

2. The shield structure according to claim 1 wherein the syringe end of the body portion has a cavity opening away from the vial end for conforming to and guidingly accepting a portion of a syringe as the cannula on a syringe is directed through the internal holding chamber towards the vial.

3. The shield structure according to claim 1 wherein said vial has a neck and said connecting means comprises a cap at the vial end of the body portion that can be placed over a vial neck and a locking ring surrounding the cap on a vial neck in an assembled position for the shield structure and vial to maintain the cap on a vial neck.

4. The shield structure according to claim 1 wherein said body portion is made from a moldable plastic material.

5. The shield structure according to claim 1 wherein said second means comprises an imperforate self-sealing wall that is penetrable by the cannula.

6. The shield structure according to claim 1 wherein the holding chamber is defined at least partially by a wall on the body portion intermediate the syringe end and vial end and having an opening extending completely therethrough, a sealing member is provided, and means mount the sealing member on said wall so that the sealing member seals the opening in the wall, said sealing member being readily penetrable by the cannula and self-sealing upon removal of the cannula from the body portion.

7. The shield structure according to claim 1 wherein a bleeder vent is provided, means mount the bleeder vent to the body portion for communication between the holding chamber and the atmosphere, said bleeder vent permitting pressure reduction in the holding chamber, and filter means are provided in the vent for filtering harmful materials attempting to escape from the holding chamber.

8. The shield structure according to claim 1 wherein a cylindrical sleeve is provided, means are provided for attachment of the cylindrical sleeve to the syringe, and means are provided for mating said sleeve closely telescopingly with the body portion for guiding movement of the syringe toward and away from the vial.

9. The shield structure according to claim 2 including a deformable annular ring and means for fixedly seating the annular ring in the cavity in the syringe end of the body portion, said ring engageable with the syringe for sealing between the syringe and the body portion.

10. The shield structure according to claim 3 wherein said vial has an enlarged rim defining a shoulder, said vial end of the body portion has a cylindrical configuration and a radially inwardly projecting rib, said locking ring compressibly forcing the rib into radially overlapping relationship with the shoulder in the assembled position of the shield structure and vial to prohibit axial separation of a vial and the shield structure.

11. The shield structure according to claim 10 wherein said vial end of the body portion has a plurality of axial slits which permit axial compression of the cap and allow expansion of the cap radially outwardly to assist placement of the vial end of the body portion over the vial neck.

12. The shield structure according to claim 1 wherein a sleeve portion is integrally formed on the syringe end of the body portion, the sleeve portion of the body has an arm axially extending from the sleeve portion for engaging a flange on a syringe to retain the syringe and the cannula in a fixed position relative to the body portion.

13. The shield structure according to claim 3 wherein notches are formed on the cap for preventing the locking ring from backing off of said cap.

14. The shield structure of claim 1 wherein means are formed on said body portion for retaining a syringe barrel in a fixed position relative to the shield structure.

15. The shield structure as claimed in claim 14 wherein a closure is tethered to said retaining means, said closure seating in the end of the syringe barrel during storage and shipment of the shield assembly.

16. The shield structure as claimed in claim 15 wherein said closure has an arm integrally formed on said sleeve portion.

17. The shield structure as claimed in claim 16 wherein at least one notch is formed in said arm for engaging with a flange on said syringe barrel to retain the syringe in a fixed predetermined position.

18. A vial assembly for connection with a syringe having a cannula and an associated fluid retaining barrel with an outer surface, to allow delivery of solution into and withdrawal of solution from a vial without exposure of a user of the syringe to the solution, said vial assembly comprising:

a vial having a chamber for retaining a supply of solution;

a septum on said vial penetrable by said cannula;

a shield structure having a syringe end, a vial end and a surface defining a fluid holding chamber;

means for connecting the shield structure to the vial so that the holding chamber surface and vial septum cooperatively define a fluid tight internal holding chamber and for permitting the syringe to be entirely separated from the shield structure, said vial chamber and internal holding chamber being substantially sealed from each other by the septum to prevent inadvertent passage of solution in said vial chamber into the holding chamber; and first means at the syringe end of the shield structure for removably admitting the cannula into the holding chamber, for self-sealing to maintain said holding chamber fluid tight to prevent the passage of fluid out of the fluid tight holding chamber upon removal of the cannula from the holding chamber and separation of the cannula from the shield structure, and for preventing the solution from contacting the outer surface of the barrel wherein it might be contacted by a user of the syringe, said fluid tight internal holding chamber capturing solution that escapes from the vial during filling of the vial and upon withdrawal of the cannula with its associated barrel from the vial said syringe being usable in conventional manner upon being separated from said shield structure to administer the solution in the barrel to a patient and without exposing a user of the syringe to the escaped solution.

19. The vial assembly according to claim 18 wherein means are provided at the syringe end of the shield structure for accepting and guiding a portion of the syringe as the cannula is directed relative to the body portion towards and away from the holding chamber and said first means comprises a sealing member on a surface bounding the cavity.

20. The vial assembly according to claim 18 wherein a seal is provided and means removably attach the seal at the syringe end of the shield structure to prevent contamination of the holding chamber.

21. The vial assembly according to claim 20 wherein said cannula has a fixed hub, there is a cavity at the syringe end of the body to receive the fixed hub, the cavity is defined by a peripheral wall and said peripheral wall has a plurality of ribs extending into the cavity, there being means on the hub to engage said ribs so that the ribs are grippingly engaged with the hub and the barrel can be rotated relative to the hub with the cannula hub pressed into the cavity to tighten the cannula hub onto the barrel.

22. A method of mixing a solution in and drawing a liquid solution from a chamber in a vial having a protective septum using a syringe with a cannula and an associated barrel and aspirating a portion of the solution outside the vial without exposing a user to the aspirated portion of the solution, said method comprising the steps of:

attaching a shield structure that is entirely separable from the syringe and vial which shield structure comprises a cap having a surface defining a fluid holding chamber with an opening that is sealed by the vial septum with the shield structure and syringe attached to make the holding chamber fluid tight and wherein the septum prevents inadvertent communication of solution between the holding chamber and the vial chamber;

moving the syringe relative to the shield structure having the holding chamber and thereby extending the cannula through a self-sealing member, through the fluid tight internal holding chamber, through the septum and into the vial;

discharging a first medicament from the syringe into a second medicament in the vial;

mixing the first and second medicaments to form a liquid solution;

drawing the liquid solution from the vial into the syringe barrel through the cannula;

pulling the cannula out of the septum of the vial so that the discharge end of the cannula is situated in the fluid tight internal holding chamber;

expelling a portion of the solution in the syringe into the fluid tight internal holding chamber so that the expelled solution is safely confined in the holding chamber; and removing the syringe including the cannula and barrel from the shield structure through said self-sealing member so that the syringe and shield structure are completely separated, one from the other, and so that the syringe is available for intravenous injection of the solution in a conventional manner.

23. A method of drawing a liquid solution from a chamber in a vial having a protective septum using a syringe with a cannula and an associated barrel and aspirating a portion of the solution outside the vial without exposing a user to the aspirated portion of the solution, said method comprising the steps of:

attaching a shield structure that is separable from the syringe and vial and comprises a cap which in conjunction with the vial septum defines a fluid tight holding chamber bounded partially by said vial septum onto the vial in fluid tight relation so that the septum blocks communication of solution from the vial chamber into the holding chamber;

moving the syringe relative to the shield structure having the holding chamber and thereby extending the cannula through a self-sealing member on the shield structure, through the fluid tight internal holding chamber, through the septum and into the vial;

drawing liquid solution from the vial into the syringe barrel through the cannula;

pulling the cannula out of the septum of the vial so that the discharge end of the cannula is situated in the fluid tight internal holding chamber;

expelling a portion of the solution in the syringe into the fluid tight internal holding chamber; and separating the syringe including the cannula and barrel as a unit from the shield structure, whereby said syringe can be used in conventional manner to administer the solution in the barrel to a patient and said fluid tight internal holding chamber substantially confines the expelled portion of the solution safely away from the syringe user.

* * * * *

UNITED STATES PATENT AND TRADEMARK OFFICE
CERTIFICATE OF CORRECTION

PATENT NO. : 5,088,996

DATED : February 18, 1992

INVENTOR(S) : RUDOLPH J. KOPFER

It is certified that error appears in the above-identified patent and that said Letters Patent is hereby corrected as shown below:

On the cover page, column 1, line 3, Item [76] Inventors: lines 5 and 6, the name "Robert E. Smith" and the address "P.O. Box 2999, Ketchum, Id. 83350" should be deleted.

Patent, column 1, line 1, the spelling of the title of the invention should be corrected "Anti-Aersoling" should be -- Anti-Aerosoling -- .

Column 2, line 30, "The" should be -- the --.

Column 2, line 36, a comma -- , -- should appear after "member".

Column 2, line 47, a period -- . -- should appear after "cannula".

Column 3, line 28, "can" should be -- cap --.

Column 4, line 56, a comma -- , -- should appear after "alternative".

Column 4, line 58, "to" should be -- so --.

Column 5, line 53, "of" should be -- on --.

UNITED STATES PATENT AND TRADEMARK OFFICE
CERTIFICATE OF CORRECTION

PATENT NO. : 5,088,996

DATED : February 18, 1992

INVENTOR(S) : RUDOLPH J. KOPFER

It is certified that error appears in the above-identified patent and that said Letters Patent is hereby corrected as shown below:

Column 6, line 15, "[he" should be -- the --.

Column 8, line 34, "52" should be -- 352 --.

Column 9, line 46, a period -- . -- should appear after "attached".

Column 9, line 47, "84" should be -- 684 --.

Column 10, line 48, a period -- . -- should appear at the end of the line.

Column 11, line 8, "838" should be -- 808 --.

Signed and Sealed this

Tenth Day of May, 1994

Attest:

BRUCE LEHMAN

*Attesting Officer*

*Commissioner of Patents and Trademarks*